United States Patent [19]

Cobb

[11] Patent Number: 5,473,934
[45] Date of Patent: Dec. 12, 1995

[54] ULTRASONIC FLUID COMPOSITION MONITOR

[76] Inventor: Wesley Cobb, 2592 S. Belvoir, University Heights, Ohio 44118

[21] Appl. No.: 135,530

[22] Filed: Oct. 13, 1993

[51] Int. Cl.⁶ .......................... G01N 29/02; G01N 29/28
[52] U.S. Cl. ........................... 73/61.49; 73/597; 73/644
[58] Field of Search ........................... 73/61.41, 61.79, 73/61.45, 61.49, 579, 599, 61.43, 61.44, 861.04, 597, 644

[56] References Cited

U.S. PATENT DOCUMENTS

| | | | |
|---|---|---|---|
| 3,602,036 | 8/1971 | Peterson | 73/644 |
| 3,663,842 | 5/1972 | Miller | 73/644 |
| 3,791,200 | 2/1974 | Hayre | 73/61.79 |
| 4,014,373 | 4/1977 | Freeman et al. | 73/597 |
| 4,022,058 | 5/1977 | Brown | 73/597 |
| 4,080,837 | 3/1978 | Alexander et al. | 73/61.45 |
| 4,232,548 | 11/1980 | Baumoel | 73/597 |
| 4,522,068 | 6/1985 | Smith | 73/32 A |
| 4,656,869 | 4/1987 | Zacharias | 73/597 |
| 4,852,396 | 8/1989 | Tavlarides | 73/61.45 |
| 5,060,507 | 10/1991 | Urmson et al. | 73/24.01 |
| 5,076,094 | 12/1991 | Frye et al. | 73/597 X |
| 5,245,290 | 9/1993 | Cannon et al. | 73/597 |
| 5,255,564 | 10/1993 | Glad et al. | 73/61.79 X |

FOREIGN PATENT DOCUMENTS

| | | | |
|---|---|---|---|
| 0233047 | 8/1987 | European Pat. Off. | 73/61.49 |
| 0250559 | 10/1988 | Japan . | |

OTHER PUBLICATIONS

C. Tsouris & L. Tavlarides, "Volume Fraction Measurements of Water in Oil by an Ultrasonic Technique," Ind. Eng. Chem. Res. 1993, 32, 998–1002.

*Primary Examiner*—Hezron E. Williams
*Assistant Examiner*—Michael J. Brock
*Attorney, Agent, or Firm*—Leydig, Voit & Mayer

[57] ABSTRACT

A method of and apparatus for continuous monitoring of the composition of a fluid mixture traveling through a conduit. The relative component concentration of the fluid mixture of a liquid/liquid or solid/liquid mixture is monitored with a non-intrusive ultrasonic apparatus. The relative component concentration of the fluid mixture is determined by measuring ultrasonic propagation parameters and temperature and comparing these measured parameters to calibrated data based on analytical measurements of samples of the process fluid mixtures. The calibrated data is obtained by measuring propagation parameters and analyzing process fluid mixtures at a different time from the measurements of process fluid mixtures.

6 Claims, 4 Drawing Sheets

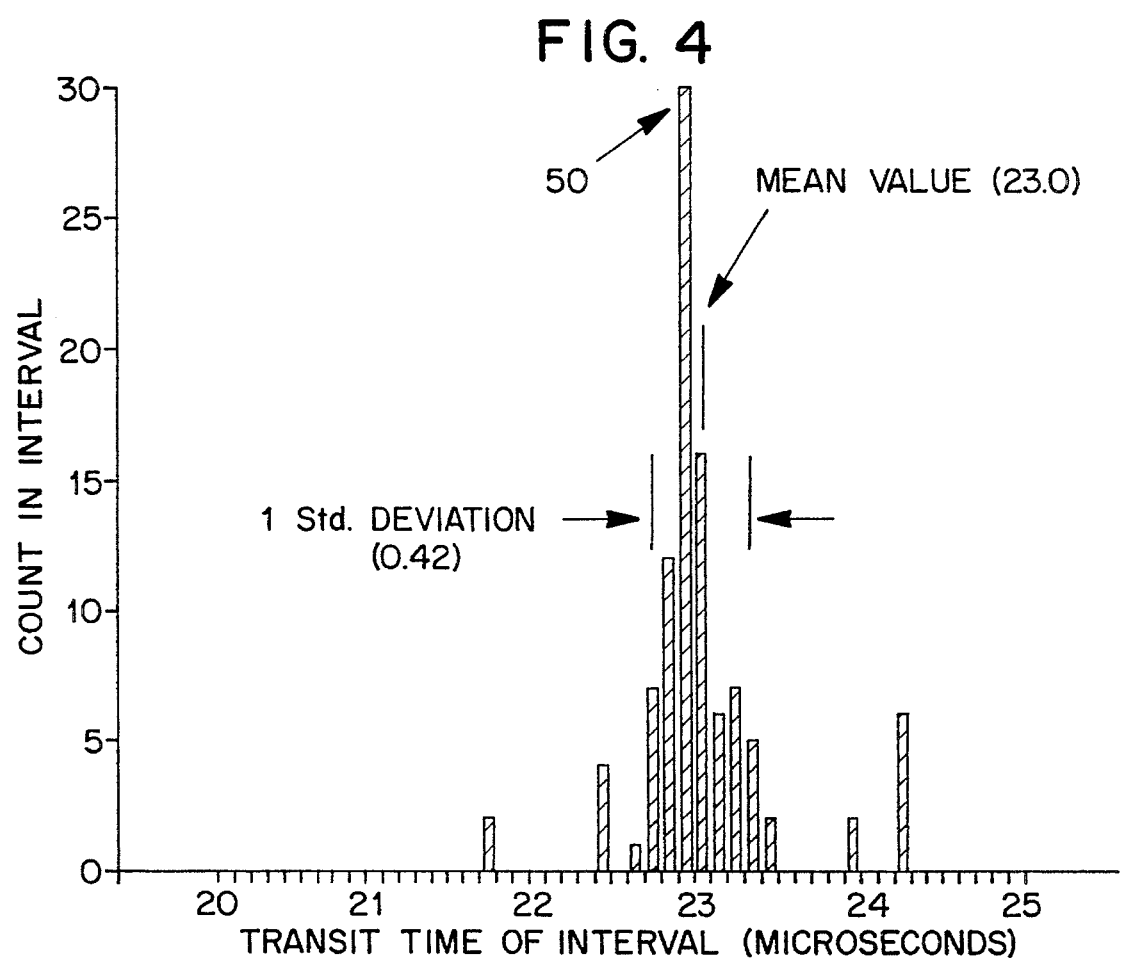

ULTRASONIC FLUID COMPOSITION MONITOR

FIELD OF THE INVENTION

This invention relates to a method and apparatus for monitoring the composition of a liquid/liquid or liquid/solid mixture traveling through a conduit. More specifically, the invention relates to a system in which ultrasonic energy signals are used to monitor the composition of such mixtures including a fluid.

BACKGROUND OF THE INVENTION

Ultrasonic monitoring techniques and apparatus for determining the composition of fluids are known. For example, U. S. Pat. No. 5,060,507 describes an apparatus that monitors fluid mixtures by comparing acoustic travel-times of both changing and reference fluid samples. U.S. Pat. No. 4,852,396 uses sonic velocity measurements made through windows in the side of a reactor to determine the fractional volumes of the liquid components of a two-liquid mixture in the reactor. Measured data for each of the two components are known. U. S. Pat. No. 4,522,068 describes use of ultrasonic transducers in a vessel to determine the density of a liquid slurry within the vessel. A method of measuring the composition of an oil and water mixture in a flowing pipeline is described in U.S. Pat. No. 4,656,869. The speeds of sound transmission in the pipeline and in the separate liquids are used to determine the water/oil ratio.

Previously, monitoring of fluid composition using ultrasonics has been attempted using transducers mounted directly in the fluid flow or through special windows machined into the wall of a conduit or vessel. These approaches are all subject to fouling of the sensors or windows by the fluid, making these systems ineffective for long-term, maintenance-free operation. Similarly, the intrusion of the transducers can result in contamination of the process being measured or disruption of the flow pattern in the conduit.

Systems described in the prior art are calibrated off-line by filling the space between transducers with reference fluids of known composition, measuring the transit time or sound speed of the known fluids, and then establishing a relationship between these measurements and the known fluid composition. The derived relationship is later used to convert the measurements into the composition of a mixture. The calibration is difficult due to the need to separate individual fluid components or prepare fluid samples of known composition. In addition, to obtain a suitable calibration relationship, the sample measurements must be obtained over a range of fluid pressure and temperature conditions that covers the range of pressures and temperatures of the process being monitored. In practice, the need to contain and measure the characteristics of fluid samples under process conditions can make the calibration expensive and difficult.

Those skilled in the art readily understand the wide range of potential applications for composition monitoring of fluids flowing in a conduit in various industries such as food, pharmaceuticals, chemicals, petroleum, waste treatment, and paper. Fluid composition is an important indicator of the quality of many industrial processes. An important application of ultrasonic monitoring in is the determination of the quality of a process separating oil and water in the petroleum industry. In this application, it is desirable to monitor low levels of water left in a fluid mixture stream after various separations and prior to the combination, transit, and sale of the fluid as crude oil. By monitoring the water content of the mixture at various stages and locations of the separation process, the separation process can be optimized and excess water content minimized.

SUMMARY OF THE INVENTION

Accordingly, it is an object of this invention to provide a method and apparatus for non-intrusive monitoring of the composition of liquid/liquid and liquid/solid mixtures, i.e., mixtures including a fluid, flowing through a conduit that avoids the drawbacks of the prior art.

It is also an object of this invention to provide a technique for measuring mixture composition in which a transducer configuration and coupling improve the detection of ultrasonic, i.e., acoustical, waves that travel through conduit walls and the mixture being monitored.

It is another object of this invention to provide a technique for measuring the composition of a fluid mixture, i.e., a mixture including a fluid, with non-intrusive transducers that can be easily moved between different locations on a conduit carrying the fluid mixture without modification of the conduit.

As a further object and feature of the invention, a novel method of processing ultrasonic signals is provided that improves the precision of the ultrasonic measurement of propagation parameters of a fluid mixture. Accurate analysis of multiple signals is used to reduce the effects of noise on the measurements. This analysis reduces the effects of random electronic noise and interference produced by ultrasonic waves scattered by bubbles and particles in the fluid mixture.

Still another object of the invention is to provide a method for on-line calibration of the monitoring apparatus that does not require the preparation of samples of known composition. An important feature of this calibration method is the direct manner in which the calibration can be maintained during changes in the ultrasonic properties of the components of the fluid mixture.

The foregoing objects are achieved by measuring three propagation parameters of an ultrasonic pulse transmitted through conduit walls and through a fluid mixture contained in the conduit. The three parameters are peak signal amplitude, transit time, and the differential transit time of two initial portions of an ultrasonic pulse. These propagation parameters are used in computing fluid mixture composition.

The ultrasonic signal is generated and received by transducers mounted on delay lines that are in contact with the conduit. These delay lines are preferably contoured to maximize the signal received after passing through the fluid mixture and minimize interfering signals that travel around the conduit rather than through the fluid in the conduit and complicate the analysis of the received signal.

The fluid mixture composition is determined by positioning a transducer assembly on a conduit, measuring ultrasonic propagation parameters and temperature of the fluid mixture. These data are used to determine fluid mixture composition from a relationship derived from analytical measurements of samples of the fluid mixture taken at the same time parameter measurements are made in a calibration procedure. The ultrasonic pulses are produced by one of the transducers and either pass directly across the conduit to a receiving transducer or are reflected and returned to the sending transducer. A circuit is connected to the transducers for electrically exciting the transducer or transducers, amplifying the received signal, determining the propagation parameters, and computing the fluid mixture composition.

BRIEF DESCRIPTION OF THE DRAWING FIGURES

A fuller understanding of the invention will be had from the following detailed description taken in conjunction with the accompanying drawing figures. In all of the drawing figures, the same elements are given the same reference numbers.

FIG. 1b is a cross-sectional view taken along line 1b–1b of FIG. 1a.

FIG. 4 is a histogram showing the number of transit-time measurements within a time interval.

DETAILED DESCRIPTION OF THE PREFERRED EMBODIMENTS

Figure 1A:
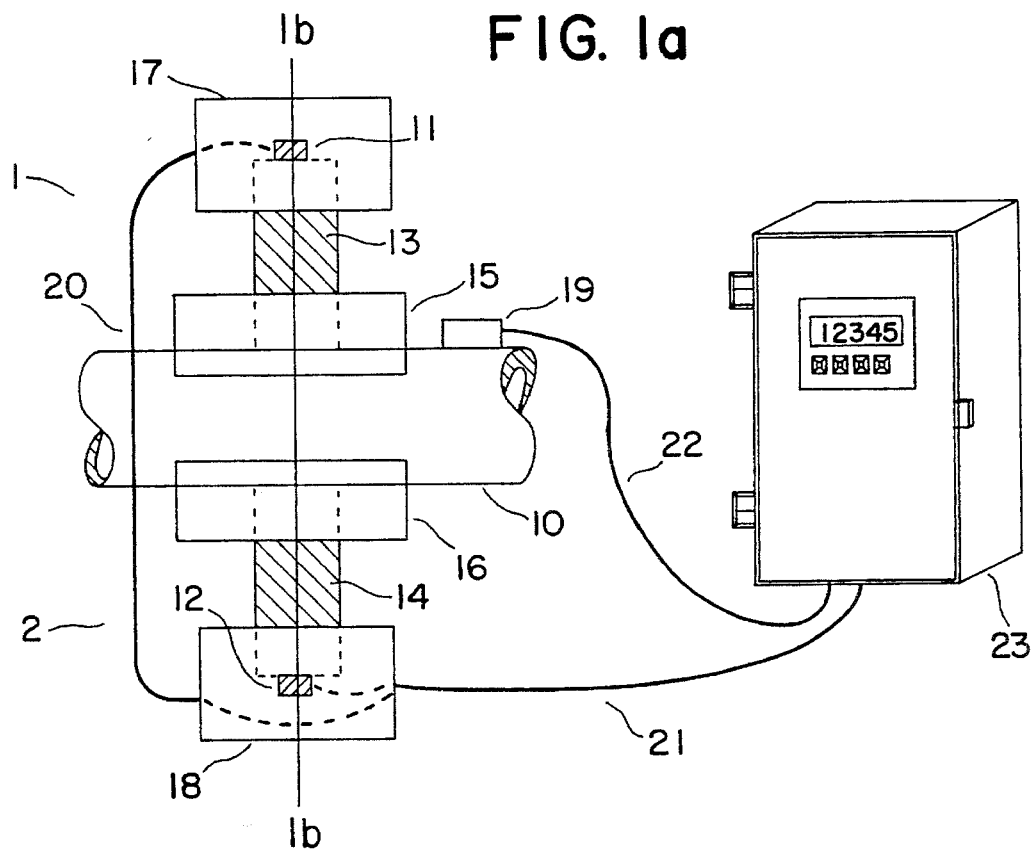
FIG. 1a is a view of an embodiment of an apparatus according to the invention.

FIG. 1a is a partially schematic view of two ultrasonic transducer assemblies 1 and 2 mounted on the outside of a conduit or pipe 10. Ultrasonic waves are produced in a transmitting transducer 11 in response to an electrical signal applied to the transducer. The ultrasonic waves either pass directly across the conduit 10 to a receiving transducer 12 or are reflected and returned to the transmitting transducer 11. In the latter case, the second transducer assembly 2 is not needed because the waves reflect from the conduit inner wall opposite the transmitting transducer. The conduit 10 may be made of any material that will carry the ultrasonic signals to the fluid mixture inside. A fluid mixture includes at least one fluid, such as a liquid, and at least one additional component that may be a different fluid or a solid. The conduit 10 may have any diameter or wall thickness. Larger conduits will provide a longer ultrasonic path through the fluid mixture and will result in a more precise measurement of mixture composition. However, a longer path will also result in a greater attenuation of the ultrasonic waves, particularly for highly absorptive fluid mixtures. Larger attenuation can prevent the reception of a measurable ultrasonic signal.

Transducer assemblies 1 and 2 respectively include transducers 11 and 12, delay lines 13 and 14, and mounts 15 and 16. The transducer assemblies can be attached on opposite sides of the conduit 10 at the same longitudinal location with straps, clamps, or other mechanical means. The arrangement shown in FIG. 1a provides the advantage of a device that is non-intrusive to the conduit. With this arrangement, the transducer elements, delay lines, and mounts are isolated from the fluid mixture in the conduit 10 and cannot be fouled. Unlike an arrangement that uses ultrasonic windows to couple waves to the fluid, the arrangement of FIG. 1a permits the transducer assemblies 1 and 2 to be easily removed and repositioned at various locations on the conduit 10.

As shown in FIG. 1a, the delay line 13 is used to carry ultrasonic waves from transmitting transducer 11 to the conduit 10. Ultrasonic waves propagating through the fluid mixture and the conduit 10 continue through the mount 16 and the delay line 14 to reach the receiving transducer 12. The delay lines 13 and 14 can be made of any material that will carry ultrasonic waves. The delay lines allow the transducer elements 11 and 12 to be enclosed in protective housings 17 and 18, respectively, such as explosion-proof housings supplied by Crouse-Hinds of Syracuse, N.Y. With this arrangement, the transducer elements 11 and 12 and their electrical leads can be isolated from the environment outside the apparatus. Isolation may be important for protection of the transducer elements and for meeting electrical safety codes in hazardous locations. The apparatus of FIG. 1a also includes a non-intrusive temperature sensor 19 attached to the conduit 10 for sensing the temperature of a fluid mixture in the conduit 10. Cables 20, 21, and 22 respectivly connect the transducers 11 and 12 and the temperature sensor 19 to an electronic control system 23 that can also be enclosed in a protective housing for use in hazardous locations.

In accordance with an important feature of the invention, the delay lines 13 and 14 have surfaces adjacent the conduit 10 that conform with the surface of the conduit. The conformal delay line and conduit surfaces maximize coupling between the conduit and ultrasonic waves and reduce the amplitude of the conduit-borne waves. For a cylindrical conduit, this condition is met if the delay line surface has a radius of curvature substantially equal to the radius of curvature of the outer conduit wall. In this structure, the gap between the delay line surface and the conduit wall will be minimized. The gap is typically filled with a grease or other fluid to conduct the ultrasonic waves between the coupling block and the conduit.

Figure 1B:
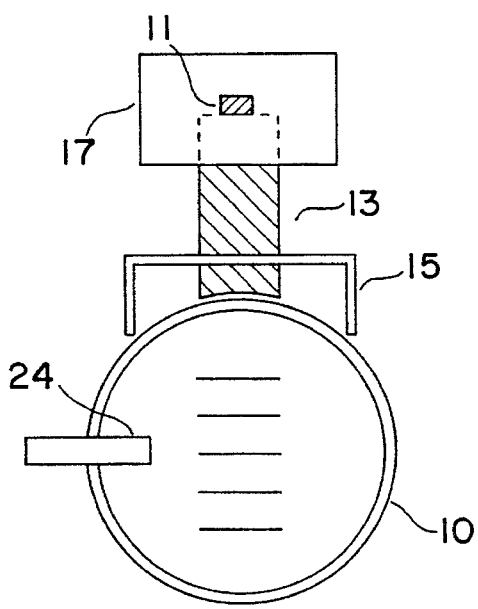

To illustrate the curvature of the delay lines 13 and 14, FIG. 1b shows a cross-sectional view of the transducer assembly 1 and the conduit 10 taken along line 1b–1b of FIG. 1a. For simplicity, only the transducer assembly 1 mounted to the top of the conduit 10 is shown. In FIG. 1b, as an alternative, the non-intrusive temperature probe 19 of FIG. 1a is replaced by an intrusive temperature sensor 24 that extends through the wall of the conduit 10 and directly contacts a fluid mixture in the conduit 10 to measure the temperature of the fluid mixture. In hazardous applications of the apparatus, the temperature sensor can be shielded from the fluid by enclosing it in a "Thermowell," such as supplied by Thermo Electric of Saddle Brook, N.J.

Figure 1C:
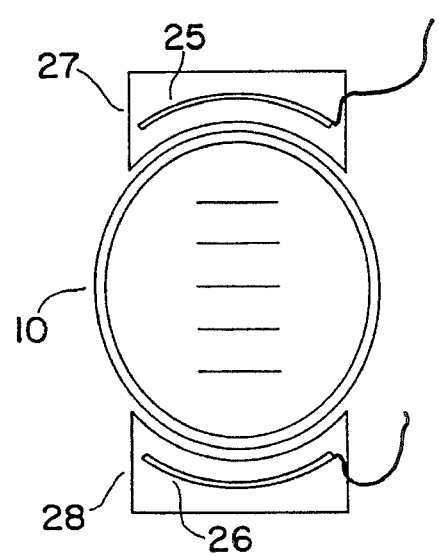
FIG. 1c is a cross-sectional view of sensor mounts in a second embodiment of the invention.

FIG. 1c illustrates another embodiment of the invention that improves the detection of the fluidborne waves by reducing the conduit-borne waves. In this embodiment, curved transducer elements 25 and 26 are mounted inside housings 27 and 28 respectively, that are attached to the conduit 10. To minimize the conduit-borne waves, the radius of curvature of each of the housings is the same as the radius of the conduit plus the separation between the elements 25 and 26 and the conduit 10.

Figure 2A:
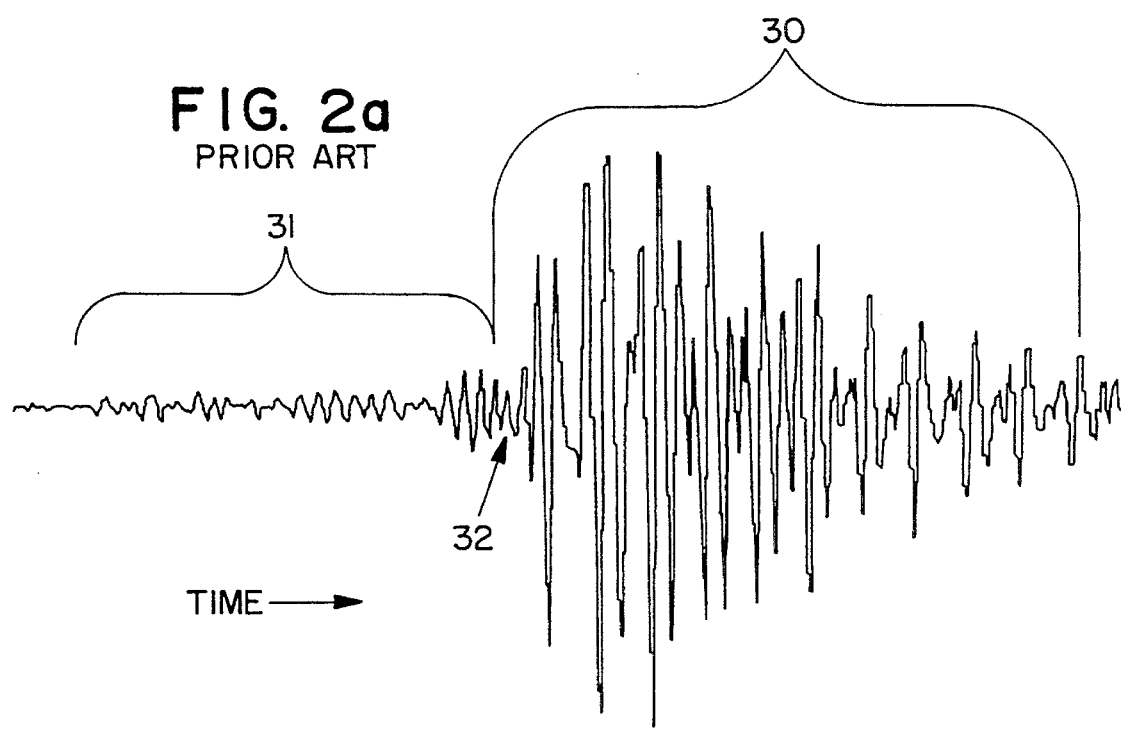
FIG. 2a is a graph of the amplitude of a received longitudinal wave as a function of time as detected using a prior art apparatus.
Figure 2B:
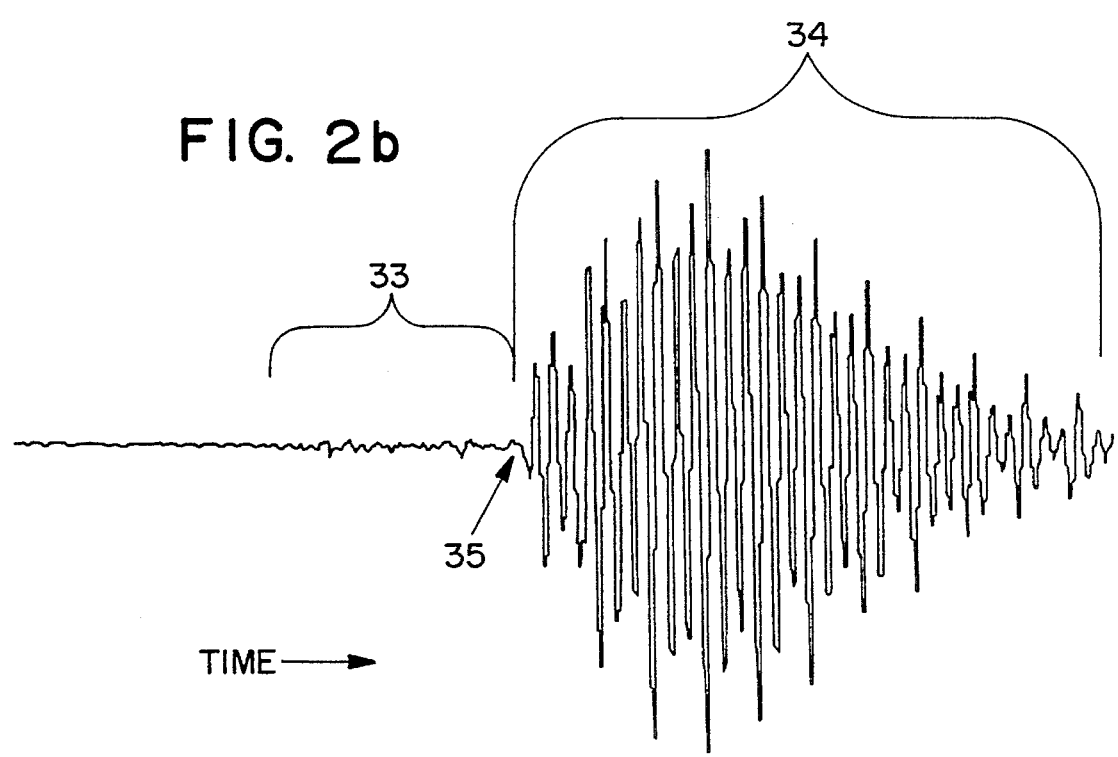
FIG. 2b is a graph of the amplitude of a received longitudinal wave as a function of time as detected using an apparatus according to an embodiment of this invention.

FIGS. 2a and 2b illustrate the waveforms of ultrasonic waves passing through a water-filled stainless steel pipe with a 3 inch inner diameter and a 0.216 inch wall thickness. The amplitudes of the waves are plotted as a function of time based on an electrical signal produced by the receiving transducer.

FIG. 2a shows an example ultrasonic waveform detected over time using a pair of planar transducers. The transducers are mounted on opposite sides of a conduit of circular cross-section at the same longitudinal position along the conduit. The transducers include a planar sensor element with a planar protective facing material. A coupling fluid is used to carry the ultrasonic waves from the transducer face to the conduit surface. As shown in FIG. 2a, the waveform is the sum of the waves traveling directly through the water and interfering waves that travel only through the conduit wall. The direct wave propagating through the water is an oscillating wave with an amplitude that increases to a peak value and then decreases over time. The invention relies on the detection of an initial portion 32 of a fluid mixture-borne wave 30 to determine the transit time and amplitude of the signal passing through the fluid mixture. The ultrasonic waves 31 that travel through the conduit wall have varying amplitudes and arrive at the receiver at varying times before and after the arrival of the wave passing through the fluid mixture. As illustrated in FIG. 2a, the conduit-borne waves interfere with the fluid mixture-borne waves and complicate the detection of the initial portion 32 of the fluid mixture-borne wave 30.

FIG. 2b is an example of the waveform detected for the mechanical arrangement and curved-end delay lines illustrated in FIGS. 1a and 1b. As indicated in that figure, the amplitude of the received waves 33 that travel around the walls of the conduit without passing through the fluid mixture is significantly reduced relative to the amplitude of the wave 34 that passes through the fluid mixture. Through the use of the delay line, the initial portion 35 of the fluid-borne wave 34 can be clearly detected relative to the interfering, conduit-borne waves.

Figure 3:
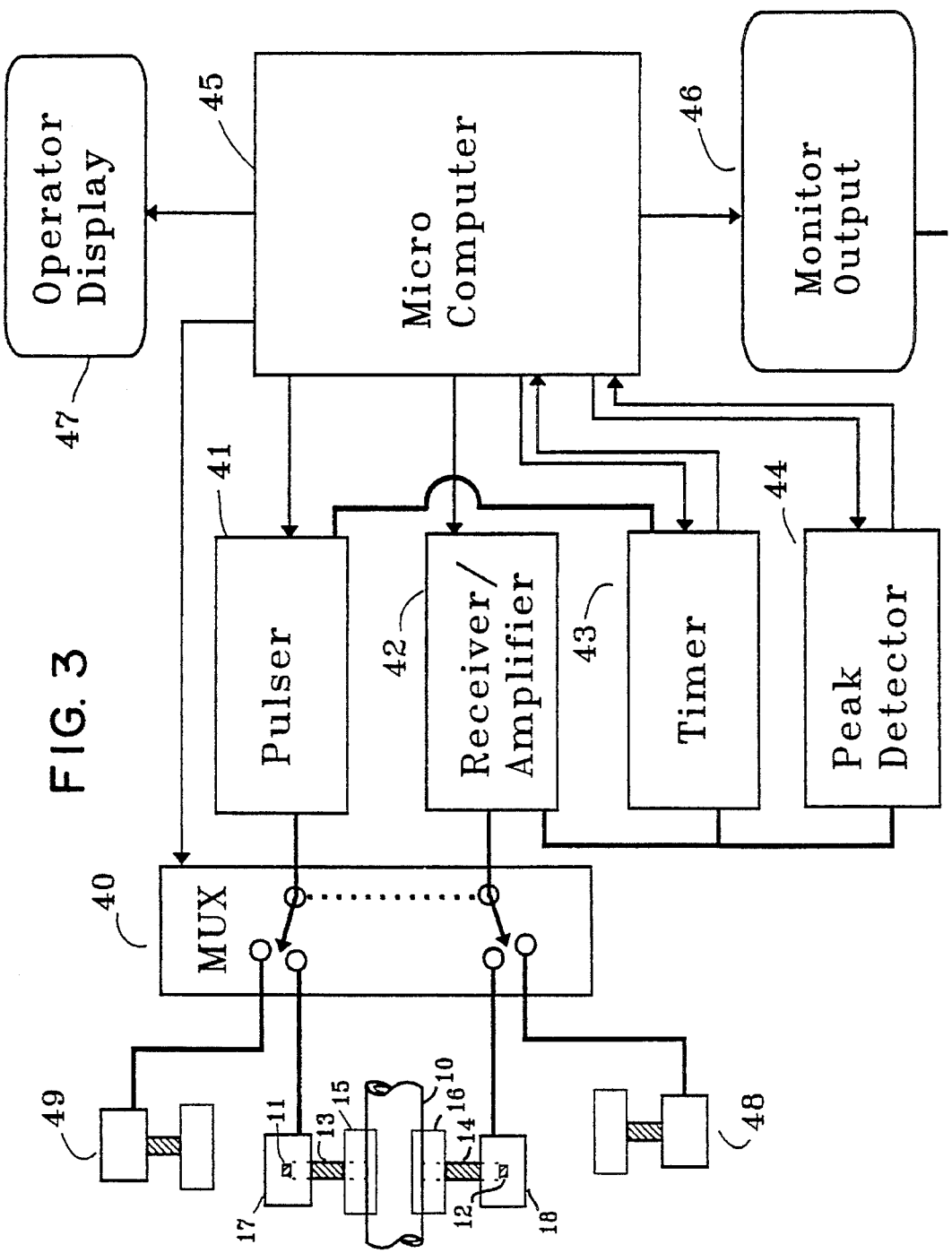
FIG. 3 is a schematic block diagram of an apparatus according to an embodiment of the invention.

The apparatus shown in FIG. 3 processes the electrical signals produced in response to ultrasonic waves generated by the transmitting transducer 11 and detected by the receiving transducer 12. A multiplexer 40 selects which of several transducers, located at different composition measurement locations on the conduit, is used as the transmitter for a given measurement. A transduce can be used for transmitting only or for both transmitting and receiving ultrasonic waves. For a single transducer transmitter/receiver, the multiplexer 40 is used to connect the transducer element directly to a pulser 41 and a receiver/amplifier 42. For separate transmitter-receiver pairs, multiplexer 40 is used to select the receiving and transmitting transducer pair for a given measurement, for example, transducer pair 11 and 12 or 48 and 49. The pulser 41 energizes the transmitting transducer with high frequency (e.g., 1–10 MHz), short duration (e.g., 1–10 microseconds) pulsed ultrasonic waves that serially pass through the delay line 13, the wall of the conduit 10, a fluid mixture in the conduit 10, the wall of the conduit 10, and the delay line 14 to be received by the receiving transducer 12. A microcomputer 45 controls the rate of pulse generation and amplitude of pulses produced by the pulser 41. The pulse amplitude is in the range of 5 to 500 volts, preferably with a rise-time between 5 and 50 nanoseconds.

Ultrasonic waves detected by the receiving transducer 12 are converted to electrical signals that are input to the receiver/amplifier 42 where the signals are amplified. An amplified signal is input to both a timer 43 and an ultrasonic peak detector 44. The microcomputer 45 adjusts the gain of receiver/amplifier 42 so that the peak amplitude of the received signal has a suitable value for proper operation of the timer 43 (e.g., 1.0 volt). Frequent adjustment of the gain of the receiver/amplifier 42 compensates for ultrasonic wave attenuation changes in the fluid mixture. The receiver/amplifier 42 also eliminates portions of the received signal that are outside the expected time range for reception of the fluid mixture-borne waves. A peak detector 44 measures the peak amplitude of the ultrasonic waves within the time period that a received signal is expected to be present at the receiving transducer. Digital indications from both the timer 43 and the peak detector 44 are sent to the microcomputer 45 for further processing. Fluid mixture composition is calculated in the microcomputer 45 based on the received ultrasonic waves and output by the monitor output unit 46. The result of the fluid mixture composition determination can also be viewed on a display 47.

The apparatus of FIG. 3 is used to measure several characteristics of the received waves that relate to the propagation of ultrasonic waves through the fluid mixture. First, the amplitude of the received signal is recorded as a measure of the attenuation of the fluid mixture. The amplitude of the received signal, $V_s$, is measured as:

$V_s = V_0/G$ where $V_0$ is the peak amplitude of the received signal produced by the received waves and G is the gain factor required to obtain the desired peak amplitude, as described previously.

A second propagation parameter measured by the apparatus is the transit time of the ultrasonic waves. The transit time is determined by the timer 43 under control of the microcomputer 45. Upon initiation of each pulse of ultrasonic waves launched by the transmitting transducer 11, the timer 43 starts counting internally generated, high-frequency clock pulses. When the pulse of ultrasonic waves is received by the transducer 12 and the amplitude of the electrical signal produced in response to the received waves exceeds a positive threshold value (e.g., 0.1 volt), the timer 43 is stopped and the time interval between starting and stopping of the timer is recorded as the transit time. An equivalent time interval measurement is also made and recorded for a negative threshold value. The smaller of the two measured time intervals is the transit time of the ultrasonic waves between the transducers through the fluid mixture.

In order to increase the accuracy of the transit-time measurement, multiple transit-time measurements are taken and averaged. A set of transit-time measurements (e.g., 100 measurements) is taken and averaged during a time when the fluid composition in the conduit 10 is not expected to change.

A third propagation parameter measured by the apparatus is the differential transit time. That parameter is continuously monitored by the apparatus. The differential transit time is the difference between the larger and smaller transit times described previously. For a substantially sinusoidal received signal, the larger transit time will be recorded for the next half cycle of the received signal after the shorter transit time. Thus, the two transits of interest of the received signal will have opposite polarities and the difference between them is the differential transit time.

The differential transit time is an important parameter of ultrasonic wave propagation in the fluid mixture in the conduit because it is a measure of the frequency-dependent absorption of the ultrasonic waves in the fluid mixture. For most fluid mixtures, the higher frequency components of a short-duration wave are preferentially absorbed in passing through the fluid mixture. This preferential attenuation lowers the center frequency of the received waves and increases the differential transit time. The differential transit time parameter can therefore be used to measure the fluid mixture composition in a manner similar to the measurement of the transit time. Use of the differential transit time has the advantage that the need for temperature compensation is avoided. The differential transit time parameter is measured only from the initial portion of a received signal. The differential transit time measurement does not rely on later received portions of the received signal that may contain confounding signals due to multiple received waves, including waves passing through the conduit walls and waves scattered by obstacles in the fluid mixture.

An important feature of the invention is the processing of multiple transit-time measurements to remove the effects of gas bubbles or solid particles in the fluid. These unwanted gas bubbles and particles scatter ultrasonic signals passing through the fluid mixture. For large bubbles or particles, ultrasonic waves may be severely scattered and the amplitude of the received waves may fail to produce an electrical signal reaching the threshold level. In this case, the measured transit time will be out of range or will correspond to the detection of waves scattered by bubbles or particles. When a great deal of gas is present in the fluid, a suitable signal for determining transit time may only occur infrequently within the expected time period for arrival of the fluid mixture-borne ultrasonic waves at the receiving transducer 12.

Digital processing of received signals is used to screen out transit-time values recorded in the presence of gas bubbles or particles. FIG. 4 illustrates the screening process in an example histogram of a set of transit-time measurements when gas bubbles or large solid particles repeatedly interrupt the passage of the ultrasonic waves through a fluid. In this histogram, the number of the transit-time measurements within each of a number of small transit-time intervals is plotted versus the center value of each interval. For this example, any transit-time values shorter than 20 microseconds and longer than 25 microseconds are eliminated by the receiver/amplifier 42 as outside a reasonable time range for receiving signals. As illustrated in FIG. 4, the largest number of counts occurs in an interval 50 that includes the transit time for passage of the ultrasonic waves only through the fluid mixture. Transit-time counts outside this interval correspond to ultrasonic waves scattered by gas bubbles and/or solid particles. Including these transit times in the calculation of the average transit time would lead to an incorrect average value for the transit time through the fluid mixture.

The microcomputer 45 is used to calculate the mean and standard deviation of the transit-time set. FIG. 4 shows the mean transit time and measured transit times within one standard deviation of the mean transit time. To obtain the average transit-time value, all transit-time measurements in the set are averaged except those outside a range that is centered about the mean value. The preferred range is one standard deviation of the distribution centered on the mean transit time, as illustrated in FIG. 4. The screening of the transit-time values outside that preferred range results in a more accurate transit-time determination for the fluid mixture-borne ultrasonic waves, yet allows the mean transit time to vary slowly in response to changes in fluid mixture.

The apparatus is calibrated while the transducer assemblies are clamped to the outside of the conduit. The ultrasonic parameter measurements are made and stored by the apparatus in non-volatile memory at the same time a sample is taken of the fluid mixture. The concentrations of the components in the sample are determined and later input into the apparatus in a memory location previously established for holding measurements for a given fluid mixture sample. These concentrations can be previously known or can be obtained through laboratory analysis of the samples.

The known calibration data are compared to the measurements to determine the composition of the fluid mixture. The temperature and ultrasonic wave propagation parameters are correlated with the analyzed fluid mixture compositions. These data are then available for use in interpreting measured data for fluid mixtures of the same components that are not subjected to chemical or like analysis for a determination of the composition of the fluid mixture.

For the calibration to be accurate over a large range of process conditions, samples of the fluid mixture should be taken for wide variations in fluid mixture concentration and temperature. In addition, the sampling point on the conduit should be as close as possible to the sensor mount to obtain a sample that is representative of the fluid mixture through which the ultrasonic waves are transmitted. The fluid mixture composition must be relatively constant over the time interval required to extract the sample and make the ultrasonic wave measurements.

Since the transit-time measurements are sensitive to temperature, the fluid mixture temperature is measured. The temperature measurements are used to correct the calculation of fluid mixture composition for temperature changes. For fluid mixtures with slowly varying temperatures, the conduit walls will be near thermal equilibrium with the fluid mixture, and a temperature sensor, like sensor 19 in FIG. 1a, external to and mounted on the conduit 10, is used to monitor fluid temperature. The external temperature sensor can be clamped to the wall of the conduit or mounted on a delay line. The sensor housing should be covered with insulation to minimize the effect of temperature changes in the environment outside the conduit. For processes with rapid fluid mixture temperature changes, a temperature sensor inserted directly into the fluid mixture, such as temperature sensor 23 of FIG. 1b, should be used. Small fittings or "thermowells" are preferably present along the conduit for this purpose.

The relative component concentration C of a fluid mixture is obtained from the ultrasonic parameter measurements using the relationship of Equation (1).

$$C = K_0 + K_1*P + K_2*T + K_3*P^2 + K_4*T^2 + K_5*P*T \qquad (1)$$

where P is one of the measured propagation parameters, T is the measured temperature, and $K_0 \ldots K_5$ are calibration coefficients obtained from a multiple regression analysis. The regression analysis can be performed using a calibration data set including the stored parameter data and input concentration measurements for the samples discussed above. Alternatively, the regression analysis for the calibration coefficients can be performed by a separate computer with the coefficients input for calibration and later calculation of fluid mixture composition.

An example of a calibration used in an embodiment of the invention, is shown in Table 1. A calibration data set of the transit-time propagation parameter for mixtures of glycerin in distilled water contained in a one inch conduit is listed in Table 1.

TABLE 1

| Prepared Concentration (approx Glycerin % by Vol.) | Transit-Time (microseconds) | Temperature (Fahrenheit) |
| --- | --- | --- |
| 25 | 29.724 | 73.5 |
| 33 | 29.277 | 76.9 |
| 50 | 28.983 | 76.9 |
| 75 | 28.160 | 73.4 |
| 25 | 29.495 | 92.3 |

TABLE 1-continued

| Prepared Concentration (approx Glycerin % by Vol.) | Transit-Time (microseconds) | Temperature (Fahrenheit) |
|---|---|---|
| 33 | 29.085 | 92.3 |
| 50 | 28.817 | 92.2 |
| 75 | 28.056 | 92.4 |

When a multiple linear regression is performed using this calibration data set and Equation (1), the calibration coefficients $K_0 \ldots K_5$ of Table 2 are obtained. Table 2 also includes the correlation coefficient and standard error of the regression, indicating its quality. The well known procedures for multiple linear regression analysis are described in *Numerical Methods for Engineers*, S. C. Chapra, McGraw-Hill, New York, and other publications.

TABLE 2

| | Variable | Value |
|---|---|---|
| $K_0$ | Constant | 1676.2625 |
| $K_1$ | Tof | −87.5986 |
| $K_2$ | Temp | 3.5456 |
| $K_3$ | Tof$^2$ | 1.1583 |
| $K_4$ | Temp$^2$ | 0.0053 |
| $K_5$ | Tof*Temp | −0.1651 |

Correlation Coefficient (r) = 0.990
Standard Error of Estimate (SEE) = 5.47

The regression coefficients determined in the calibration are used to interpret measured data and thereby determine the composition of a fluid mixture. For example, the measured transit-time parameter for an approximately 66% glycerin-in-water mixture was 28.395 microseconds at 92.3 degrees Fahrenheit. When these data and the calibration coefficients of Table 2 are entered into Equation (1), a fluid mixture concentration of 62.5% is computed. The error, 69% versus 62.5%, is primarily due to inaccuracies in the prepared sample concentrations used in the calibration.

Using the Equation (1) above, any one of the ultrasonic propagation parameters can be used to determine the fluid mixture composition. The preferred parameter for a given application can be preselected based on prior knowledge of the fluid mixture or established empirically through testing the measurement performance of the apparatus for each parameter. In general, the preferred parameter will be the one that is most sensitive to composition changes, yet is least affected by confounding process changes (e.g., aeration and temperature fluctuations).

The on-line calibration technique has the advantage that the calibration can be easily updated. If the ultrasonic propagation characteristics of the individual fluid mixture components change, additional propagation parameters and sample data can be included with the previous calibration data set. The regression analysis is then repeated with the updated data set and the new calibration coefficients are used to calculate component concentration.

In a second embodiment of this invention, the calibration relationship for the transit-time parameter is computed from the sound speeds and dimensions of the delay line material, conduit, and fluids of known composition. With transducers positioned on opposite sides of the conduit, the transit time parameter $P_2$ can be calculated as:

$$P_2 = 2*D_{cd}/S_{cd} + 2*D_{cw}/S_{cw} + D_f/S_f$$

where $D_{cd}$, $D_{cd}$, and $D_f$ are known ultrasonic wave propagation distances in the delay line material, the conduit wall, and the fluid mixture, respectively. $S_{cd}$ and $S_{cw}$ are the known or measured sound speeds in the delay line material and the conduit wall, respectively. The sound speeds, $S_f$, of respective fluid mixture samples of known composition, are measured at several temperatures near the expected temperature of the fluid mixture in the conduit. The transit times ($P_2$) for each of several fluid mixture compositions and temperatures are then used as the calibration data set in the multiple regression calculation to determine the calibration coefficients, $K_0 \ldots K_5$.

The above-described calibration technique for the transit-time parameter has the advantage that the calibration can be completed before the transducers are mounted on the conduit. This preliminary calibration can then be improved by including on-line transit-time measurements and sample analysis in a new calibration data set. The regression analysis is then repeated with the updated data set and the new calibration coefficients are used to calculate component concentrations of the fluid mixture.

The invention has been described with respect to certain preferred embodiments. However, various additions and modifications within the spirit of the invention will occur to those of skill in the art. Accordingly, the scope of the invention is limited by the following claims and not by the foregoing description.

I claim:

1. An apparatus for monitoring the composition of a fluid mixture flowing through a conduit comprising:

a transducer assembly for clamping on an outside wall of a conduit;

means for launching ultrasonic waves through the wall of the conduit and a fluid mixture having at least two components and flowing within the conduit;

means for detecting an ultrasonic wave that has been launched and has passed through the fluid mixture and for converting the detected ultrasonic wave into an electrical signal indicative of first and second transit times through the fluid mixture from two initially received, sequential, opposite polarity portions of the detected ultrasonic wave;

means for computing first and second transit times and a differential transit time by subtracting the second transit time from the first transit time and for computing the relative concentrations of the components of the fluid mixture from predetermined relationships between fluid mixture composition and differential transit time; and means for indicating the computed relative concentration.

2. The apparatus of claim 1 wherein the transducer assembly includes a transducer element having a non-planar surface shaped to conform to the outside wall of the conduit.

3. The apparatus of claim 1 wherein said transducer assembly includes an ultrasonic delay line having an end surface shaped to conform to the outside wall of the conduit.

4. The apparatus of claim 3 wherein the delay line has a concave end surface for conforming to a cylindrical conduit.

5. The apparatus of claim 1 wherein said means for launching includes a first ultrasonic transducer and said means for detecting includes a second ultrasonic transducer.

6. The apparatus of claim 1 wherein said means for launching and said means for detecting include a common ultrasonic transducer for launching and detecting ultrasonic waves.

* * * * *